United States Patent [19]

Malhotra et al.

[11] Patent Number: 4,776,880
[45] Date of Patent: Oct. 11, 1988

[54] DIPHENOXYMETHYLPYRIDINES

[75] Inventors: Sudarshan K. Malhotra, Walnut Creek; Ingrid L. Knox, Antioch, both of Calif.

[73] Assignee: The Dow Chemical Company, Midland, Mich.

[21] Appl. No.: 150,592

[22] Filed: Feb. 1, 1988

Related U.S. Application Data

[60] Continuation-in-part of Ser. No. 933,502, Nov. 21, 1986, abandoned, which is a division of Ser. No. 814,840, Dec. 30, 1985, Pat. No. 4,685,953, which is a division of Ser. No. 656,834, Oct. 2, 1984, Pat. No. 4,606,757, which is a continuation-in-part of Ser. No. 452,584, Dec. 23, 1982, abandoned.

[51] Int. Cl.⁴ ............... C07D 401/04; A01N 43/40
[52] U.S. Cl. ............................. 71/92; 71/94; 546/194; 546/21; 546/276; 546/301; 546/302; 546/286; 546/339
[58] Field of Search ............... 546/276; 71/92

[56] References Cited

U.S. PATENT DOCUMENTS

| | | | |
|---|---|---|---|
| 4,163,787 | 8/1979 | Malhotra et al. | 514/345 |
| 4,221,799 | 9/1980 | Van Heertum et al. | 514/345 |
| 4,256,893 | 3/1981 | Malhotra et al. | 546/301 |
| 4,262,001 | 4/1981 | Malhotra et al. | 514/338 |
| 4,324,896 | 4/1982 | Malhotra et al. | 546/301 |
| 4,351,943 | 9/1982 | Malhotra et al. | 546/301 |

Primary Examiner—Alan L. Rotman
Attorney, Agent, or Firm—S. Preston Jones; Ronald G. Brookens

[57] ABSTRACT

Disclosed are diphenoxymethylpyridines, their preparation and their use as herbicides.

6 Claims, No Drawings

DIPHENOXYMETHYLPYRIDINES

CROSS-REFERENCE TO RELATED APPLICATIONS

The present application is a continuation-in-part of application Ser. No. 933,502 filed Nov. 21, 1986, abandoned which is a Divisional of application Ser. No. 814,840 filed Dec. 30, 1985, now U.S. Pat. No. 4,685,953, which is a Divisional of application Ser. No. 656,834 filed Oct. 2, 1984, now U.S. Pat. No. 4,606,757 which in turn is a continuation-in-part of application Ser. No. 452,584 filed Dec. 23, 1982, now abandoned.

SUMMARY OF THE INVENTION

The present invention is directed to compounds corresponding to the formula

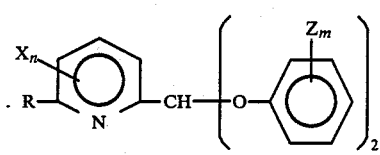

wherein R represents hydrogen, alkyl of 1 to 4 carbon atoms, hydroxyalkoxy of 1 to 4 carbon atoms, alkoxy of 1 to 4 carbon atoms, alkenyloxy of 2 to 4 carbon atoms, alkylthio of 1 to 4 carbon atoms, alkoxyalkoxy wherein each alkoxy group independently contains from 1 to 4 carbon atoms, chloro or fluoroalkoxy of 1 to 4 carbon atoms, cyano, aminomethyl, monoalkylamino of 1 to 4 carbon atoms, dialkylamino with each alkyl group independently being of 1 to 4 carbon atoms, piperidinyl, morpholino, the radical

wherein A is oxygen or sulfur and $R^1$ is alkyl of 1 to 4 carbon atoms or R represents triazolyl or the radical

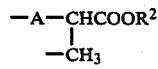

wherein $R^2$ is hydrogen or alkyl of 1 to 4 carbon atoms; X represents bromo, chloro or fluoro; n represents an integer of 0 or 1 with the proviso that when R is hydrogen, n is 0: Z represents bromo, chloro, fluoro, alkylthio of 1 to 4 carbon atoms or alkoxy of 1 to 4 carbon atoms and m represents an integer of 0 or 1.

In the present specification and claims, the terms "alkyl" and "alkoxy" as employed in the terms alkyl, alkoxy, alkylthio, fluoroalkoxy, alkoxyalkoxy monoalkylamino and dialkylamino designate straight-chain, branched-chain or cyclic alkyl groups.

The terms "chloroalkoxy" and "fluoroalkoxy" as employed in the present specification and claims designates an alkyl group as defined above which is substituted with from 1 chloro or fluoro atom up to perchloro or perfluoro substitutions.

The term "halo" as employed in the present specification and claims designates either bromo, chloro or fluoro.

The term "triazolyl" as employed in the present specification and claims to represent 1,2,3-, 1,2,4- and 1,3,4-triazolyl groups.

The substituted pyridine compounds of the employed present invention are either solids or liquids which are only slightly soluble in water and are usually moderately to highly soluble in common organic solvents. The compounds of the present invention have been found to be very effective pre- and/or post-emergent herbicides for the control of one or more plant species.

The compounds of the present invention can be prepared by a variety of methods. For example, those compounds wherein R is hydrogen can be prepared by the catalytic hydrogenation of an appropriate 6-halo-2-((diphenoxy or substituted diphenoxy)methyl)pyridine in the presence of a solvent.

While any suitable hydrogenation procedure can be employed in carrying out this hydrogenation reaction, it is convenient to mix a catalytic amount of from about 0.1 to about 10 percent by weight of the catalyst, the pyridine reactant, a solvent and an HCl absorber together and then pass hydrogen into the mixture. It is also convenient to use a sealed reaction vessel.

Representative catalyst include any of the conventional hydrogenation catalyst such as platinum or palladium on charcoal. Representative solvents include ethanol, methanol, toluene or ethyl acetate.

The reaction is usually carried out at a temperature of from about 15° C. to about 30° C. and at a pressure in the range of from about 50 psig. The reaction is usually complete in from about 3 to about 8 hours.

After the reaction is complete, the reaction mixture is filtered to remove the catalyst and other insolubles and then concentrated by evaporation of the solvent under reduced pressure. The concentrate is mixed with dilute sodium hydroxide and extracted with a solvent such as methylene chloride, ether, methylchloroform or chloroform. The extract is washed with water, dried and the solvent removed by conventional techniques such as decantation or evaporation. The crude product which remains is distilled to remove lower boiling impurities and recovering the desired product.

Those compounds wherein R is alkyl, alkoxy or cyano can be prepared by the reaction of one mole of the appropriate 6-alkyl, 6-alkoxy or 6-cyano-2-(dichloromethyl)pyridine is reacted with 2 moles of the appropriate phenol in the presence of a solvent and an alkali metal hydroxide such as the sodium, potassium, lithium or cesium hydroxide. The reaction scheme is as follows:

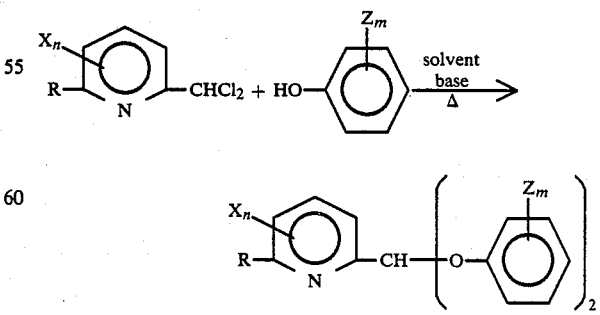

In the above, R is alkyl, alkoxy or cyano and X, Z, n and m are as hereinbefore defined. No attempt has been made to present a balanced equation.

In carrying out this reaction, the pyridine reactant and the salt of the phenol are mixed together in the presence of a solvent and heated to a temperature of from about 100° to 200° C. and stirred for from about 2 to about 24 hours. Thereafter, the reaction product is cooled, diluted with water and extracted with a solvent such as for example, 1,1,1-trichloroethane, methylene chloride, chloroform, ethyl acetate or ethyl ether. The solvent extract is water washed, dried and concentrated under reduced pressure and, if desired, purified by distillation or other conventional methods.

The reaction consumes the reactants in stoichiometric proportions, i.e., one molar equivalent of the pyridine reactant to 3 molar equivalents of the phenol reactant. However, due to the nature of the reaction, it is preferred that a 5 to 25 percent excess of the phenol reactant be employed.

While the above procedure shows the use of an already prepared alkali metal salt of the phenol, this salt can be prepared in situ. In such a procedure, the pyridine reactant, an appropriate substituted methoxy phenol and an alkali metal hydroxide are mixed together with the solvent and then heated as set forth hereinabove. The alkali metal hydroxide is employed in a molar amount equal to that employed for the phenol reactant.

Representative solvents for use in carrying out this reaction include dimethyl sulfoxide, dimethylformamide, N-methyl-2-pyrrolidone, toluene and xylene.

Those compounds wherein R is alkoxy, hydroxyalkoxy, alkoxyalkoxy, fluoroalkoxy or alkylthio can be prepared by the reaction of an appropriate 6-halo-2-((diphenoxy or substituted phenoxy)methyl)pyridine with an appropriate alcohol or thioalcohol in the presence of a solvent and a base. The reaction scheme is as follows:

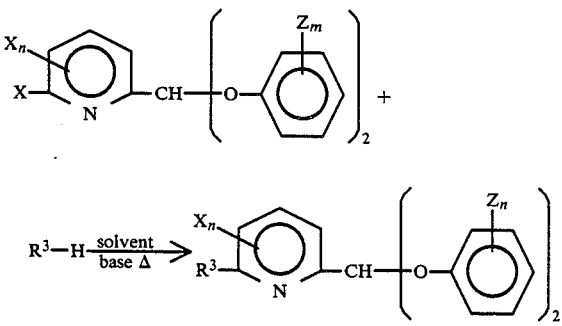

In the above X, Z, n and m are as hereinabove defined and $R^3$ is alkoxy, hydroxyalkoxy, alkoxyalkoxy, or alkylthio. Additionally, no attempt has been made to present a balanced equation.

In carrying out the reaction, the reactants can be mixed in any suitable fashion. Usually, the $R^3$—H reactant is mixed with the base and the pyridine reactant, in the solvent, is added thereto.

Representative solvents which can be employed in the reaction include dimethylsulfoxide (DMSO), sulfolane, dimethylformamide (DMF) and dioxane.

Representative bases which can be employed include the metal, hydroxide or hydrides of sodium or potassium. The reaction is carried out by heating the mixture at a temperature in the range of from about 25° to about 100° C. for from about 16 hours to about 24 hours or more.

At the completion of the reaction, the reaction mixture is poured into water or a water-alcohol mixture and then extracted with a solvent such as methylene chloride, methylchloroform, ether or chloroform. The solvent/organic layer is separated and washed with water, dried, filtered to remove insolubles and the solvent removed by evaporation under reduced pressure. The product is then recovered by distillation.

The reaction consumes the reactants in stoichiometric proportions, i.e., one molar equivalent of the pyridine reactant to one molar equivalent of the $R^3$—H reactant. However, due to the nature of the reaction it is preferred that a 5 to a 100 percent excess of the $R^3$—H reactant be employed. The base is employed in an amount of 1.0 to 1.2 molar equivalents per equivalent of the alcohol or thio alcohol.

Those compounds wherein R is alkenyloxy can be prepared by the reaction of an appropriate 6-hydroxy-2-di-(phenoxy or substituted phenoxy)pyridine with an alkenyl halide in the presence of a solvent and an alkali metal hydrogen halide absorber.

In carrying out this reaction, it is convenient to first mix the hydroxypyridine reactant with an alkali metal hydride such as sodium hydride at room temperature in a solvent such as dimethylsulfoxide, sulfolane, dioxane or dimethylformamide to convert the hydroxy group to the reactive NaO— group. The alkenyl halide is then slowly added, with stirring. The reaction is usually complete in from about 1 to about 2 hours. After the completion of the reaction, the reaction mixture is diluted with water and extracted with a solvent such as methylene chloride, chloroform, methylchloroform or ether. The extract is dried and the solvent is removed. The product can be recovered from the residue by conventional techniques such as distillation under reduced pressure.

The reaction consumes the reactants in stoichiometric proportions, i.e., one molar equivalent of the pyridine reactant to one molar equivalent of the alkenyl halide reactant. However, due to the nature of the reaction it is preferred that a 5 to 100 percent excess of the alkenyl halide reactant be employed. The base is employed in an amount of 1.0 to 1.3 molar equivalents per equivalent of the pyridine reactant.

Those compounds wherein R is chloro or fluoroalkoxy or

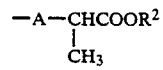

can be prepared by the reaction of an appropriate 6-hydroxy(or mercapto)-2-((diphenoxy or substituted diphenoxy)methyl)pyridine with an appropriate $R^4$—Cl (or Br) compound wherein $R^4$ is chloro or fluoro alkoxy or a propionic acid ester in the presence of a solvent and a base. The reaction procedure, the base and the solvent are the same as set forth above. The reaction scheme is as follows:

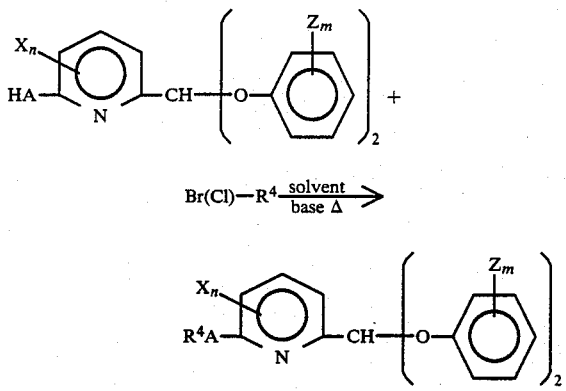

In carrying out the reaction, the reactants can be mixed in any suitable fashion. Usually the pyridine reactant in solvent is mixed with the alkali metal hydride to convert the hydroxy group to the reactive NaO—group. The bromo (or chloro) —R⁴ reactant is then added. The reaction is usually complete in from about 1 to about 4 hours. After the completion of the reaction, the reaction mixture is diluted with water and extracted with a solvent such as methylene chloride, ether, methylchloroform or chloroform. The extract is dried and the solvent is removed. The product can be recovered from the residue by conventional techniques such as distillation under reduced pressure.

The reaction consumes the reactants in stoichiometric proportions, i.e., one molar equivalent of the pyridine reactant to one molar equivalent of the propionate reactant. However, due to the nature of the reaction it is preferred that a 5 to a 100 percent excess of the propionate reactant be employed. The base is employed in an amount of 1.0 to 1.2 molar equivalents per equivalent of the pyridine reactant.

The acid form of the compound is prepared by conventional procedures wherein the ester is reacted with 50% caustic in a solvent and then acidified with an acid such as concentrated hydrochloric acid.

Those compounds wherein R is monoalkylamino, dialkylamino, piperidinyl, morpholino or triazolyl can be prepared by the reaction of an appropriate 6-chloro-2-((diphenoxy or substituted diphenoxy)methyl)pyridine with an appropriate R⁵—H compound wherein R⁵ is monoalkylamino, dialkylamino, piperidinyl, morpholino or triazolyl at a temperature of from about 50° C. to the reflux temperature of the mixture. While the reaction can be carried out neat, it can also be carried out in the presence of a solvent such as dimethylsulfoxide, sulfolane, dimethylformamide or dioxane. In addition, an alkali metal hydride such as sodium hydride can be employed to act as a hydrogen chloride absorber.

At the completion of the reaction, the reaction mixture is cooled and mixed with water and a solvent such as methylene chloride, methylchloroform, ether or chloroform. The solvent/organic layer is separated, dried and filtered to remove insolubles and the solvent removed by evaporation under reduced pressure. The product is then recovered by distillation and, if desired, it can be further purified by recrystallization from a solvent such as n-hexane or methylene chloride.

Those compounds wherein R is aminomethyl can be prepared by the reduction of an appropriate 6-cyano-2-((diphenoxy or substituted diphenoxy)methyl)pyridine to the corresponding 6-aminomethyl-2-((diphenoxy or substituted diphenoxy)methyl)pyridine employing a reducing agent such as for example lithium aluminum hydride. The reduction is carried out in the presence of a solvent and under an oxygen free atmosphere such as achieved by using nitrogen gas.

At the completion of the reaction, the reaction mixture is mixed with dilute caustic and filtered. The solvent/organic layer is separated and washed with ether, dried and the solvent removed by evaporation under reduced pressure. The resulting material can be further purified by admixture with a solvent such as methylene chloride, methylchloroform, ether or chloroform. The solvent/organic layer is filtered and the solvent removed by evaporation under reduced pressure leaving the desired product.

The reaction consumes the reactants in stoichiometric proportions, i.e., one molar equivalent of the pyridine reactant to one molar equivalent of the reducing agent. However, due to the nature of the reaction it is preferred that a 1 to 50 percent excess of the reducing agent be employed.

Those compounds wherein R is the radical

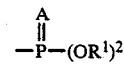

can be prepared by the reaction of an appropriate 6-hydroxy-2-((diphenoxy or substituted diphenoxy)methyl)pyridine with an appropriate chlorophosphorous compound of the formula

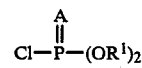

in the presence of an alkali metal compound such as sodium or potassium hydroxide or carbonate and a solvent. Representative solvents include acetone, acetonitrile, dimethylformamide, carbon tetrachloride, chloroform, benzene, toluene, isobutylmethylketone or methylene chloride.

The amounts of the reactants to be employed are not critical, some of the desired product being obtained when employing any proportions of the reactants. In the preferred method of operation, good results are obtained when employing substantially equimolar proportions of the pyridine and phosphorus reactants.

The reaction takes place smoothly at temperatures in the range of from about 0° to about 100° C. In carrying out the reaction, the reactants are mixed and contacted together in any convenient fashion and the resulting mixture maintained for a period of from about 3 to about 16 hours to complete the reaction. Following the completion of the reaction, the solvent is removed by conventional techniques such as decantation or evaporation under reduced pressure. The residue is further purified by taking the residue up in a solvent such as ether, methylene chloride or methylchloroform. The mixture is filtered to remove insolubles, washed with dilute sodium hydroxide and then with water. The organic layer is separated, dried and the solvent removed by conventional techniques leaving the desired product.

DESCRIPTION OF SOME PREFERRED EMBODIMENTS

The following examples illustrate the present invention and the manner by which it can be practical but, as such, should not be construed as limitations upon the overall scope of the same.

EXAMPLE I 2-(Diphenoxymethyl)pyridine

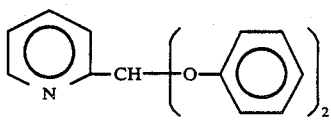

To a solution of 10.42 grams (g) (0.032 mole (m)) of 6-chloro-2-(diphenoxymethyl)pyridine, 8.02 g (0.079 m) of triethylamine in 200 milliliters (ml) of absolute ethanol in a Parr shaker bottle was added 0.5 g of 5 percent palladium on charcoal. Hydrogen was passed over the liquid surface using a Parr hydrogenator until ~3 pounds (0.3 m) had been consumed. The reaction mixture was filtered and the solvent removed by evaporation under reduced pressure. The residue was pored into a solution of 50 ml of water and 50 ml of 10 percent sodium hydroxide. This solution was extracted with methylene chloride. The extract was washed with water, dried over magnesium sulfate and the solvent stripped away under vacuum. The residue was heated at 0.02 millimeters of mercury to 110° C. to remove lower boiling impurities. The above named product was recovered as a pale yellow oil in a yield of 6.8 g and was ~99 percent pure. The Nuclear Magnetic Resonance spectrum (NMR) confirmed the product. The product has a refractive index of n25/d=1.5946 and upon analysis was found to have carbon, hydrogen and nitrogen contents of 77.78, 5.56 and 4.92 percent, respectively, as compared with the theoretical contents of 77.98, 5.24 and 5.05 percent, respectively, as calculated for the above named compound (Compound 1).

EXAMPLE II

6-Ethoxy-2-(diphenoxymethyl)pyridine

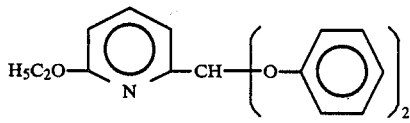

To 30.0 ml of ethanol was added 1.10 g of sodium pellets. After the sodium had dissolved, 10.14 g of 6-chloro-2-(diphenoxymethyl)pyridine in 50 ml of DMSO was added dropwise. The mixture was heated to 80° C. and held there for 24 hours. The reaction was considered complete as seen by the NMR. The reaction mixture was cooled, diluted with water and extracted with methylchloroform. The organic layer was separated and washed with water, dried over anhydrous magnesium sulfate, filtered and the solvent removed by evaporation under reduced pressure. The crude product was then distilled and the portion which distilled over at 157°-165° C. at 0.05 millimeters of mercury was collected. The above indicated product was obtained in a yield of 8.95 g and was found to have a refractive index of n26/d=1.5768. The NMR and Infrared Spectra (IR) were consistent with the structure for the above compound. Upon analysis, the compound was found to have carbon, hydrogen and nitrogen contents of 74.56, 6.01 and 4.19 percent, respectively, as compared with the theoretical contents of 74.77, 5.92 and 4.36 percent, respectively, as calculated for the above named compound (Compound 2).

EXAMPLE III

6-Methylthio-2-(diphenoxymethyl)pyridine

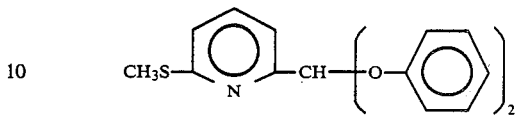

To a mixture of sodium methoxide (made from 100 ml (2.47 m) of methanol and 1.50 g (0.652 m) of sodium metal) which had been cooled to 13° C. was added 7.0 ml (0.126 m) of methylmercaptan. The mixture was allowed to warm to room temperature and then 20.0 g of 6-chloro-2-(diphenoxymethyl)pyridine and 150 ml of dimethylsulfoxide was added thereto. The mixture was heated to 90° C. and after 4 days at this temperature, the reaction mixture was cooled to room temperature and poured into 300 ml of ice. The solution was extracted with methylene chloride and the extract was dried over magnesium sulfate and the solvent stripped off under reduced pressure. The residue was further purified using preparative high pressure liquid chromatography with a 2:98 mixture of ethylacetate and hexane. The oil thus obtained crystallized in n-hexane and was purified by recrystallization from n-hexane leaving the above named compound as a white solid in a yield of 49 g (98 percent pure). The product melted at 58°-59° C. and its structure was confirmed by its NMR spectrum. Upon analysis, the product was found to have carbon, hydrogen and nitrogen contents of 70.42, 5.19 and 4.20 percent, respectively, as compared with the theoretical contents of 70.59, 5.26 and 4.33 percent, respectively, as calculated for the above named compound (Compound 3).

EXAMPLE IV 6-(2-Propenyloxy)-2-(diphenoxymethyl)pyridine

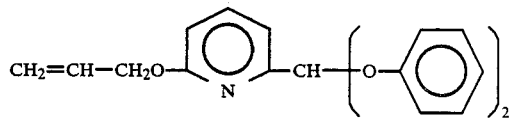

A solution of 5.0 g (0.17 m) of 6-hydroxy-2-(diphenoxymethyl)pyridine in 35 ml of dimethylsulfoxide was slowly added to 0.49 g (0.020 m) of clean sodium hydride. After the evolution of gas was completed, 1.8 ml of allylbromide was added dropwise to the mixture. After a period of two hours, the reaction mixture was poured into 50 ml of water at 25° C. and the mixture extracted with methylene chloride. The organic extract was dried over magnesium sulfate and the solvent removed by evaporation under reduced pressure. The residue was heated at 80° C. and 0.05 mm to remove low boiling impurities leaving 3.9 g of a light brown oil as the above named product. The structure of product was confirmed by its NMR. The compound had a refractive index of n25/d=1.5828. Upon analysis, the product was found to have carbon, hydrogen and nitrogen contents of 75.71, 5.91 and 4.13 percent, respectively, as compared with the theoretical contents of 75.68, 5.71 and 4.20 percent, respectively, as calculated for the above named compound (Compound 4).

EXAMPLE V

O,O-Diethyl O-(6-(diphenoxymethyl)-2-pyridinyl)-phosphorothioate

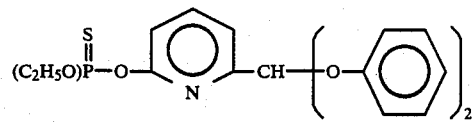

To a mixture of 5.02 g (0.17 m) of 6-hydroxy-2-(diphenoxymethyl)pyridine, 5.04 g (0.037 m) of potassium carbonate in 50.0 ml of acetonitrile was slowly added 3.21 g (0.017 m) of diethylchlorothiophosphonate. The mixture was stirred for 3½ hours. The solvent was then removed from the reaction mixture by evaporation under reduced pressure. The residue was dissolved in ether and filtered. The ether solution was washed with 5 percent sodium hydroxide and then with water. The ether layer was separated from the aqueous layer and the ether layer was dried over anhydrous magnesium sulfate. The ether was removed by evaporation leaving 6.7 g of the above indicated product as a yellow oil and in a purity of 98 percent. The product had a refractive index of n26/d=1.5660. The structure of the product was confirmed by its NMR. Upon analysis, the product was found to have carbon, hydrogen and nitrogen contents of 58.92, 5.35 and 2.95 percent, respectively, as compared with the theoretical contents of 59.33, 5.39 and 3.15 percent, respectively, calculated for the above named compound (Compound 5).

EXAMPLE VI 6-(Diphenoxymethyl)-2-pyridinenitrile (K-153705)

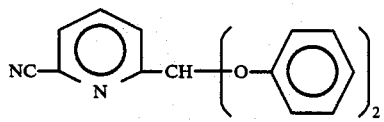

A mixture of 4.18 g of 6-cyano-2-(dichloromethyl)-pyridine, 5.25 g of phenol, 3.33 g of potassium hydroxide and 50 ml of dimethylsulfoxide was heated to 60° C. After a reaction period of about 4 hours, the reaction was complete. The mixture was cooled and poured into 100 ml of water and then extracted with methylene chloride. The solvent extract was run through a bed of silica gel and the solvent removed. The mixture was heated to 160° C. at 0.05 milliliters of mercury. The resulting material was dissolved in a mixture of about 50 ml of methylene chloride filtered and the solvent removed by evaporation under reduced pressure. The above named product was recovered in a yield of 0.95 g and melted at 82°–85° C. The structure of the product was confirmed by its NMR and IR spectrum. Upon analysis, the product was found to have carbon, hydrogen and nitrogen contents of 74.44, 4.72 and 9.05 percent, respectively as compared with the theoretical contents of 75.50, 4.64 and 9.27 percent, respectively as calculated for the above named compound (Compound 28).

EXAMPLE VII 6-(Aminomethyl)-2-(diphenoxymethyl)pyridine

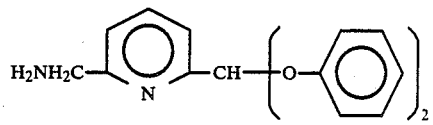

To a solution of 0.81 g of 95 percent lithium aluminum hydride in 25 ml of ether was slowly added a solution of 5.90 g of 6-cyano-2-(diphenoxymethyl)pyridine in 60 ml of ether so as to maintain a gentle reflux. The mixture was allowed to stir for about 4 hours. An additional 0.2-0.3 g of lithium aluminum hydride was added. Since no additional reaction occurred, 5 ml of water, 5 ml of 15 percent sodium hydroxide and 20 ml of water were added consecutively. The reaction mixture was filtered and the organic portion separated. The aqueous portion was washed with ether and the combined organic portions were dried over magnesium sulfate. The solvent was stripped off and the residue was dissolved in methylene chloride and then diluted with ~900 ml of hexane. The solution was passed through a silica gel column and the silica gel was rinsed with methylene chloride and then with methanol. The methanol was stripped off leaving the above named product in a yield of 3.0 grams. The structure of the product was confirmed by its NMR and IR Spectrum. Upon analysis, the product was found to have carbon, hydrogen and nitrogen contents of 72.44, 5.92 and 8.82 percent, respectively as compared with the theoretical contents of 74.51, 5.88 and 9.15 percent, respectively as calculated for the above named compound (Compound 30).

By following the appropriate preparative procedures as outlined hereinabove and in the above example and employing the appropriate starting materials, the following compounds set forth below in Table I can be prepared.

TABLE I

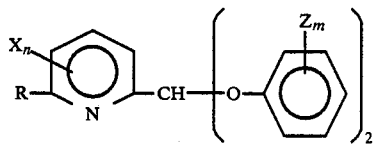

| Compound Number | R | $X_n$ | $Z_m$ | Calculated C | Calculated H | Calculated N | Found C | Found H | Found N | Physical Property RI or MP |
|---|---|---|---|---|---|---|---|---|---|---|
| 6 | —OCH₃ | —H | —H | 74.27 | 5.54 | 4.56 | 73.78 | 5.39 | 4.50 | 1.5860 |
| 7 | —OC₂H₅ | 3-F | 3-Cl | | | | | | | |
| 8 | —OC₂H₅ | 4-Cl | 4-SCH₃ | | | | | | | |
| 9 | —OCHF₂ | —H | —H | 66.47 | 4.37 | 4.00 | 66.23 | 4.30 | 3.99 | 1.5556 |

TABLE I-continued

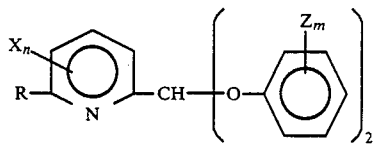

| Compound Number | R | $X_n$ | $Z_m$ | Analysis Calculated | | | Found | | | Physical Property RI or MP |
|---|---|---|---|---|---|---|---|---|---|---|
| | | | | C | H | N | C | H | N | |
| 10 | —OCH$_3$ | 5-Cl | —H | | | | | | | |
| 11 | morpholino | —H | —H | 72.93 | 6.07 | 7.73 | 71.33 | 6.13 | 7.05 | 88°–91° |
| 12 | —CH$_3$ | -3-Br | 4-n-OC$_4$H$_9$ | | | | | | | |
| 13 | OC$_4$H$_9$ | —H | —H | 75.64 | 6.59 | 4.01 | 75.42 | 6.63 | 3.90 | 1.5639 |
| 14 | piperidinyl | —H | —H | 76.67 | 6.67 | 7.78 | 75.51 | 6.69 | 7.58 | bpt 180°–190° C. at 0.02 mm |
| 15 | OCH(CH$_3$)$_2$ | —H | —H | 75.22 | 6.27 | 4.18 | 74.84 | 6.18 | 4.11 | 1.5690 |
| 16 | —N(CH$_3$)$_2$ | —H | -5-n-SC$_4$H$_9$ | | | | | | | |
| 17 | —CH$_3$ | —H | —H | 78.35 | 5.84 | 4.81 | 77.80 | 5.93 | 4.93 | 63°–66° |
| 18 | OC$_2$H$_4$OH | —H | —H | 71.22 | 5.64 | 4.15 | 70.93 | 5.75 | 4.04 | 1.5894 |
| 19 | —S—i-C$_4$H$_9$ | 4-Cl | -5-n-SC$_4$H$_9$ | | | | | | | |
| 20 | —OC$_2$H$_4$OCH$_3$ | —H | —H | 71.79 | 5.98 | 3.99 | 71.36 | 5.96 | 3.92 | 1.5717 |
| 21 | —OCH$_2$OCH$_3$ | 5-F | 3-OCH$_3$ | | | | | | | |
| 22 | —P(=O)(O—n-C$_4$H$_9$)$_2$ | 4-Cl | 4-Cl | | | | | | | |
| 23 | —OCH(CH$_3$)COOH | —H | —H | 69.04 | 5.21 | 3.84 | 64.74 | 5.01 | 3.44 | 1.5682 |
| 24 | —OCH(CH$_3$)COOC$_2$H$_5$ | —H | —H | 70.23 | 5.85 | 3.56 | 69.51 | 5.80 | 3.24 | 1.5592 |
| 25 | 1,2,4-triazol-1-yl | —H | —H | 69.77 | 4.65 | 16.28 | 70.58 | 4.69 | 14.87 | 65°–70° C. |
| 26 | NH(n-C$_6$H$_{13}$) | —H | —H | 76.60 | 7.45 | 7.45 | 75.71 | 7.44 | 7.27 | 1.5737 |
| 27 | —SCH(CH$_3$)COOH | —H | 2-SCH$_3$ | | | | | | | |
| 29 | OCHCl$_2$ | —H | —H | 62.29 | 4.27 | 3.59 | 60.64 | 3.99 | 3.72 | |

PREPARATION OF STARTING MATERIALS

Those compounds employed as starting materials and which correspond to the formula

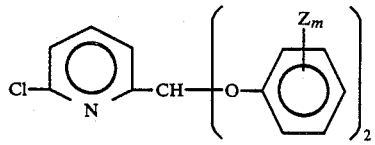

wherein Z and m are as hereinabove defined are known compounds and can be prepared as taught in U.S. Pat. Nos. 4,324,896 and 4,349,680.

Those compounds employed as starting materials and which correspond to the formula

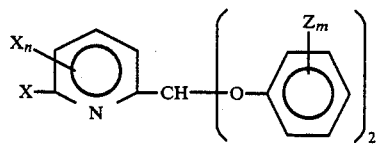

wherein X, n, Z and m are as hereinabove defined can be prepared by processes analogous to those taught in U.S. Pat. Nos. 4,324,896 and 4,349,680 wherein one mole of an appropriate 6-halo-2-(dichloromethyl)pyridine is reacted with 2 moles of an appropriate phenol.

The 6-halo-2-(dichloromethyl)pyridines employed as starting materials are known compounds and can be prepared as taught in U.S. Pat. No. 3,838,159. For those compounds wherein X is fluoro or chloro, the compounds can also be prepared as taught in U.S. Pat. No. 3,687,827.

In accordance with the present invention, it has been discovered that the diphenoxyme thylpyridine compounds of the present invention are useful as pre- and post-emergent herbicides. In accordance with this invention, a method for controlling or inhibiting the growth of undesirable plant species is provided which comprises applying to plants, plant parts or their habitat, an effective or growth inhibiting or herbicidally effective amount of at least one of the compounds as set forth hereinabove.

An outstanding feature of the present invention is the ability of the presently claimed compounds to control, either by post-emergent or pre-emergent application, the growth of one or more of the grasses and broadleaf plants, such as, for example, barnyard grass, crabgrass, yellow foxtail, wild oats, pigweed, cotton, velvet leaf, morning glory and yellow nutsedge.

The application of the compounds of the present invention to plants and plant parts and their habitats, gives rise to varying degrees of response to the compounds depending upon the nature of the plant or seed, the stage of growth or maturity of the plant, the specific compound employed, and the dosage at which plant or plant part or habitat exposure to the compound is carried out, as well as environmental conditions.

The minimum amount of active compound applied should be that which is effective in controlling and/or killing undesirable plant growth. Ordinarily, for pre-emergent control, good results are obtained when from 0.06 to 4 pounds or more of at least one of the active compounds are applied per acre. In foliage treatment, good results are obtained when from 0.02 to 4 pounds of active compound per acre are employed. In selective applications to foliage for the control of many undesirable weeds in the presence of desired crop plants, a uniform dosage of from about 0.02 to 2 pounds of active compound can be employed.

The present invention can be carried out by directly employing the claimed compounds singly or in oombination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier to produce other compositions in the form of dusts, sprays, granules, washes or drenches. In compositions where the additament is a coarsely or finely divided solid, a surface active agent or the combination of a surface active agent and a liquid additament, the added material cooperates with the active component so as to facilitate the invention. Whether the composition is employed in liquid form, as a wettable powder, or as a granular or encapsulated material, the active compound will normally be present in an amount of from about 5 to about 95 percent by weight of the total composition.

In the preparation of dust compositions, the toxicant products can be compounded with any of the finely divided solids, such as, for example, pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided clays such as, for example, attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as, for example, the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable organic liquids which can be employed in the composition include, for example, petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and active compound.

In addition, other liquid compositions containing the desired amount of effective agent can be prepared by dissolving the toxicant in an organic liquid such as, for example, acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point about 80° F. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments, the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated salicylanilides, organo sulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, P-chloro-m-cresol, sodium pentachlorophenol and other sodium, potassium, etc., salts of the phenols, substituted phenols, cresols and substituted cresols, di- and tribrominated salicylanilides, 2,2'-methylenebis(3,4,6-trichlorophenol), 2,2-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5-2H-thioadiazine-2-thione, 2,3-dinitro-1,4-dithia-anthraquinone, dodecyl pyridinium chloride, alkyl dimethylbenzylammonium chloride, dialkyl dimethylammonium chloride, bis-tributyltin oxide, bis-tripropyltin oxide, copper pentachlorophenate, copper 8-hydroxyquinolate, sodium borate, 9-undecylenic acid, 10,10'-oxybisphenoxarsine, 1-(3-chloroallyl)-3,5,7-triaza-1-azonia-adamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular oircumstances encountered, one method of application may be preferably over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water can be varied in accordance with the moisture equivalent or field capacity of the soil in order to obtain the desired depth of distribution of the toxicant.

The following embodiments are illustrative of the present methods.

EXAMPLE VII

Forty-five parts by weight of 6-ethoxy-3-fluoro-2-(bis(3-chlorophenoxy)methyl)pyridine is mixed and ground with 5 parts by weight of Triton X-155 surfactant (an alkylated aryl polyether alcohol) to prepare a water-dispersible concentrate composition containing 90 percent by weight of the ester compound.

In a further operation, 25 parts by weight of 6-methyl-3-bromo-2-(bis(4-n-butoxyphenoxy)methyl)pyridine, 10 parts by weight of Triton X-155 surfactant and 65 parts by weight of xylene are mixed together to prepare an emulsifiable concentrate composition containing 25 percent by weight of said ester compound.

A mixture of 10 parts by weight of 6-dimethylamino-2-(bis(5-n-butylthiophenoxy)methyl)pyridine, 10 parts by weight of O,O-di-n-butyl-4-chloro O-(bis(4-chlorophenoxy)methyl)-2-pyridinyl) phosphorothioate, 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water dispersible liquid concentrate composition containing 20 parts by weight of the mixed pyridine compounds. The concentrate compositions thus prepared can be dispersed in water to prepare aqueous compositions which have very desirable wetting and penetrating properties and are adapted to distribute growth inhibiting amounts of the diphenoxymethylpyridine compounds on plant parts.

EXAMPLE VIII

Representative products of the present invention were evaluated for the post-emergent control of barnyard grass, wild oats, crabgrass, pigweed, yellow foxtail and cotton. In these evaluations, plots of the above plant species grown to a height of about 4 inches were used. Aqueous spray compositions, each containing 4,000 parts of a given diphenoxymethylpyridine compound per million parts of ultimate composition, were prepared by admixing a predetermined amount of the diphenoxymethyl pyridine with a predetermined amount of a water-surfactant mixture to give an aqueous dispersion containing 4,000 parts of the compound per million parts of the ultimate dispersion. Eaoh separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table A.

TABLE A

| Compound Number | Percent Kill and Control of | | | | | |
|---|---|---|---|---|---|---|
| | Barnyard Grass | Wild Oats | Crabgrass | Pigweed | Yellow Foxtail | Cotton |
| 2 | 95 | 100 | 95 | NT | 95 | 100 |
| 3 | 100 | 100 | 95 | NT | 95 | 90 |
| 4 | 100 | 100 | 70 | 100 | — | 90 |
| 6 | 100 | 100 | 99 | — | 90 | NT |
| 9 | 100 | 100 | 100 | NT | 100 | 100 |
| 10 | 80 | 70 | 70 | — | 70 | — |
| 13 | 90 | 100 | 95 | NT | 80 | 100 |
| 17 | 75 | — | 100 | 100 | 100 | — |
| 20 | 90 | 100 | 90 | 90 | — | 70 |

TABLE A-continued

| Compound Number | Percent Kill and Control of | | | | | |
|---|---|---|---|---|---|---|
| | Barnyard Grass | Wild Oats | Crabgrass | Pigweed | Yellow Foxtail | Cotton |
| 28 | 90 | 90 | 100 | NT | — | 80 |

NT = Not Tested

In other operations carried out employing substantially the same procedures as in Example VIII, it was found that compound 15 gave 100 percent kill and control of barnyard grass and pigweeds: compounds 29 and 30 gave 100 percent kill and control of pigweeds: compounds 11 and 29 were found to give at least 70 percent kill and control of crabgrass; compound 18 was found to give at least 80 percent kill and control of wild oats and compounds 14, 18 and 20 were found to give at least 80 percent kill and control of cotton plants.

EXAMPLE IX

Additional products of the present invention were evaluated for the post-emergent control of morning glory and velvet leaf. In these evaluations, plots of the above plant species grown to a height of about 4 inches were used. Aqueous spray compositions, each containing 4,000 parts of a given diphenoxymethylpyridines compound per million parts of ultimate composition, were prepared in accordance with the procedures of Example VIII, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. It was found that each of compounds 2, 6, 9, 10, 13, 18, 20, 26, 28 and 29 gave at least 70 percent kill and control of morning glory and each of compounds 2, 3, 9, 10 and 29 gave at least 80 percent kill and control of velvet leaf.

EXAMPLE X

Aqueous compositions of various ester compounds prepared in accordance with Example VIII were employed for pre-emergent applications on plots immediately after they were seeded with crabgrass, wild oats, barnyard grass, pigweed and yellow foxtail. Other plots similarly seeded with the above plant species were treated with like compositions oontaining no toxicant to serve as control plots. The treating applications were carried out by drenching the soil with the aqueous compositions to obtain a treating rate of 10 pounds per acre. Thereafter, the plots were maintained under conditions conducive for good plant growth. Two weeks after treatment, the plots were examined to determine the percent plant growth and evaluated. The results of the examinations are set forth below in Table B.

TABLE B

| Compound Number | Percent Kill and Control of | | | | |
|---|---|---|---|---|---|
| | Barnyard Grass | Crabgrass | Yellow Foxtail | Wild Oats | Pigweed |
| 1 | 100 | 100 | 80 | — | NT |
| 2 | 100 | 100 | 100 | 100 | 100 |
| 3 | 100 | 100 | 100 | 80 | 100 |
| 4 | 100 | 100 | 90 | 100 | 100 |
| 6 | 100 | 100 | 100 | 100 | 100 |

TABLE B-continued

| Compound Number | Percent Kill and Control of | | | | |
|---|---|---|---|---|---|
| | Barnyard Grass | Crabgrass | Yellow Foxtail | Wild Oats | Pigweed |
| 9 | 100 | 100 | 100 | 100 | 100 |
| 13 | 75 | 100 | — | 80 | 100 |
| 15 | 90 | — | 80 | 90 | — |
| 17 | 100 | 100 | 100 | 100 | 100 |
| 20 | 100 | 100 | 100 | 100 | 100 |
| 24 | 95 | 95 | 70 | 98 | NT |
| 25 | — | 95 | 80 | — | 100 |
| 28 | 100 | 100 | 100 | 100 | 100 |

NT = Not Tested·

In other operations carried out employing substantially the same procedures as in Example IX, it was found that compounds 5 and 11 gave 100 percent kill and control of crabgrass and compounds 11 and 23 gave 100 percent kill and control of pigweed.

EXAMPLE XI

Aqueous compositions of various compounds prepared in a manner similar to that of Example VIII were employed for a pre-emergent applications on plots immediately after their being seeded with seeds of morning glory and velvet leaf. Other plots similarly to be seeded with the above plant species were treated with the like compositions containing no toxicant to serve as control plots. The treating applications were carried out by drenching the soil with the aqueous compositions to a depth of about one inch to obtain a treating rate of 10 pounds per acre. Thereafter, the plots were maintained under conditions conducive for good plant growth. Two weeks after treatment, the plots were examined to determine the percent plant growth and evaluated. It was found that compounds 2, 4, 6, 23 and 28 gave 100 percent kill and control of morning glory; compounds 4, 6, 9, and 28 gave 100 percent kill and control of velvet leaf and compounds 2, 3 and 20 gave at least 75 percent kill and control of velvet leaf.

PREPARATION OF STARTING MATERIALS

Those compounds employed as starting materials which correspond to the formula

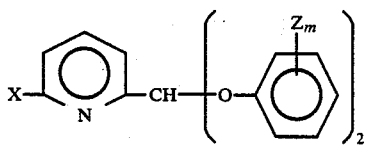

wherein X, Z and m are as defined hereinabove are all known compounds and can be prepared as taught in U.S. Pat. Nos. 4,324,896, 4,349,680 and 4,351,943.

Those compounds employed as starting materials which correspond to the formula

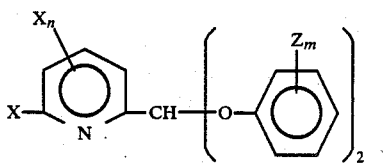

wherein X, n, Z and m are hereinbefore defined can be prepared in substantially the same manner as set forth directly above employing the appropriate substituted-2-(dichloromethyl)pyridine which are taught in U.S. Pat. Nos. 3,687,827 and 3,838,159.

Those compounds employed as starting materials which correspond to the formula

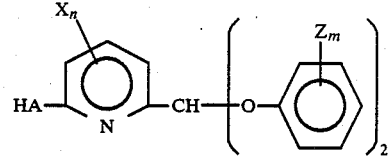

can be prepared by the reaction of an appropriate 6-halo-2-((diphenoxy or substituted diphenoxy)methyl)-pyridine with either an alkali metal hydroxide or mercaptide such as the sodium or potassium compounds (depending on whether A is oxygen or sulfur) in the presence of a solvent such as dimethylsulfoxide at a temperature of from about 80° to about 150° C. for from about 1 to 16 hours. After the completion of the reaction, the reaction mixture is diluted with water and extracted with a solvent such as trichloroethane. The aqueous layer is then acidified to about a pH 1 with concentrated hydrochloric acid and extracted with trichloroethane. The organic portions are combined, washed with water, dried and the solvent is removed to give the desired product.

What is claimed is:

1. A compound corresponding to the formula

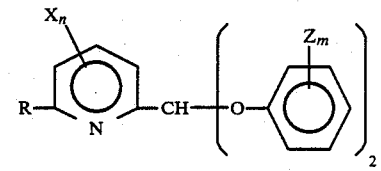

wherein R represents triazolyl: X represents bromo, chloro or fluoro: n represents an integer of 0 or 1: Z represents bromo, chloro, fluoro, alkylthio of 1 to 4 carbon atoms or alkoxy of 1 to 4 carbon atoms and m represents an integer of 0 or 1.

2. The compound as defined in claim 1 which is 2-(diphenoxymethyl)-6-(1H-1,2,4-triazol-1-yl)-pyridine.

3. A herbicidal composition which comprises an inert carrier in admixture with a herbicidally effective amount of a compound corresponding to the formula

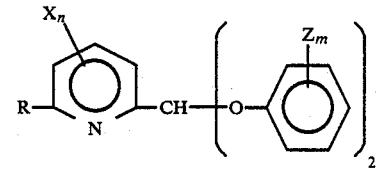

wherein R represents triazolyl; X represents bromo, chloro or fluoro: n represents an integer of 0 or 1: Z represents bromo, chloro, fluoro, alkylthio of 1 to 4 carbon atoms or alkoxy of 1 to 4 carbon atoms and m represents an integer of 0 or 1.

4. The composition as defined in claim 3 wherein the compound 2-(diphenoxymethyl)-6-(1H-1,2,4-triazol-1-yl pyridine.

5. A method for controlling the growth of undesirable plants which comprises applying to plants, plant parts or their habitat a composition which comprises an inert carrier in admixture with a herbicidally effective amount of a compound corresponding to the formula

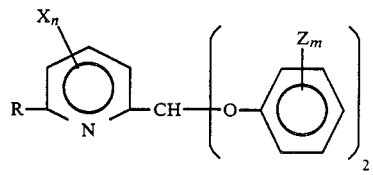

wherein R represents triazolyl: X represents bromo, chloro or fluoro; n represents an integer of 0 or 1: Z represents bromo, chloro, fluoro, alkylthio of 1 to 4 carbon atoms or alkoxy of 1 to 4 carbon atoms and m represents an integer of 0 or 1.

6. The method as defined in claim 5 wherein the compound is 2-(diphenoxymethyl)-6-(1H-1,2,4-triazol-1-yl)pyridine.

* * * * *